(12) United States Patent
Andino et al.

(10) Patent No.: US 9,700,700 B2
(45) Date of Patent: Jul. 11, 2017

(54) MEDICAL ARTICLE WITH ROTATABLE WINGS

(75) Inventors: Rafael V. Andino, Grayson, GA (US); Christopher J. Brooks, Glen Cove, NY (US)

(73) Assignee: Venetec International, Inc., Covington, GA (US)

( * ) Notice: Subject to any disclaimer, the term of this patent is extended or adjusted under 35 U.S.C. 154(b) by 435 days.

(21) Appl. No.: 13/577,425

(22) PCT Filed: Mar. 2, 2011

(86) PCT No.: PCT/US2011/026897
§ 371 (c)(1),
(2), (4) Date: Sep. 17, 2012

(87) PCT Pub. No.: WO2011/109542
PCT Pub. Date: Sep. 9, 2011

(65) Prior Publication Data
US 2013/0138080 A1    May 30, 2013

Related U.S. Application Data

(60) Provisional application No. 61/310,223, filed on Mar. 3, 2010.

(51) Int. Cl.
*A61M 25/02* (2006.01)
*A61M 25/06* (2006.01)
*A61M 25/00* (2006.01)

(52) U.S. Cl.
CPC ........ *A61M 25/02* (2013.01); *A61M 25/0015* (2013.01); *A61M 25/0606* (2013.01);
(Continued)

(58) Field of Classification Search
CPC ............ A61M 25/007; A61M 25/0637; A61M 25/0606; A61M 25/02; A61M 25/00; A61M 25/06; A61M 25/0015
(Continued)

(56) References Cited

U.S. PATENT DOCUMENTS 2,402,306 A   6/1946  Turkel
2,525,398 A  10/1950  Collins
(Continued)

FOREIGN PATENT DOCUMENTS

CA   1311977 C   12/1992
CA   1318824 C    6/1993
(Continued)

OTHER PUBLICATIONS

International Search Report from related International Application No. PCT/US2011/026897, mailed Apr. 26, 2011, in 2 pages.
(Continued)

*Primary Examiner* — Andrew Gilbert
*Assistant Examiner* — Tiffany Legette-Thompson
(74) *Attorney, Agent, or Firm* — Rutan & Tucker, LLP

(57) ABSTRACT

A medical article is configured to provide access to a patient's vasculature. The medical article includes an elongated body and a pair of stabilizing wings that extend from the elongated body and are configured to stabilize the medical article on a patient. The stabilizing wings are configured to rotate together or independently about the longitudinal axis of the elongated body between at least a first configuration and a second configuration. The elongated body can include a one-way valve disposed therein. The medical article can also one or more adhesive layers configured to releasably attach at least a portion of the wings to a patient.

19 Claims, 8 Drawing Sheets

(52) U.S. Cl.
CPC .... *A61M 25/0637* (2013.01); *Y10T 29/49817* (2015.01); *Y10T 29/49895* (2015.01)

(58) Field of Classification Search
USPC .. 604/165.03, 177, 263–264, 508, 198, 180, 604/272, 274, 247
See application file for complete search history.

(56) References Cited

U.S. PATENT DOCUMENTS

| | | | |
|---|---|---|---|
| 2,533,961 A | 12/1950 | Rousseau et al. | |
| 3,046,984 A | 7/1962 | Eby | |
| 3,064,648 A | 11/1962 | Bujan | |
| 3,167,072 A | 1/1965 | Stone et al. | |
| 3,194,235 A | 7/1965 | Cooke | |
| 3,245,567 A | 4/1966 | Knight | |
| 3,288,137 A | 11/1966 | Lund | |
| 3,394,954 A | 7/1968 | Sams | |
| 3,493,238 A | 2/1970 | Ludwig | |
| 3,529,597 A | 9/1970 | Fuzak | |
| 3,589,361 A | 6/1971 | Loper et al. | |
| 3,630,195 A | 12/1971 | Santomieri | |
| 3,677,250 A | 7/1972 | Thomas | |
| 3,686,896 A | 8/1972 | Rutter | |
| 3,766,915 A | 10/1973 | Rychlik | |
| 3,812,851 A | 5/1974 | Rodriguez | |
| 3,817,240 A * | 6/1974 | Ayres | 600/577 |
| 3,826,254 A | 7/1974 | Mellor | |
| 3,834,380 A | 9/1974 | Boyd | |
| 3,856,020 A | 12/1974 | Kovac | |
| 3,863,631 A | 2/1975 | Baldwin | |
| 3,900,026 A | 8/1975 | Wagner | |
| 3,901,226 A | 8/1975 | Scardenzan | |
| 3,906,946 A | 9/1975 | Nordstrom | |
| 3,920,001 A | 11/1975 | Edwards | |
| 3,934,576 A * | 1/1976 | Danielsson | 600/487 |
| 3,942,228 A | 3/1976 | Buckman et al. | |
| 3,973,565 A | 8/1976 | Steer | |
| 4,004,586 A | 1/1977 | Christensen et al. | |
| D243,477 S | 2/1977 | Cutruzzula et al. | |
| 4,020,835 A | 5/1977 | Nordstrom et al. | |
| 4,037,599 A | 7/1977 | Raulerson | |
| 4,059,105 A | 11/1977 | Cutruzzula et al. | |
| 4,079,738 A | 3/1978 | Dunn et al. | |
| 4,082,094 A | 4/1978 | Dailey | |
| 4,114,618 A | 9/1978 | Vargas | |
| 4,116,196 A | 9/1978 | Kaplan et al. | |
| 4,123,091 A | 10/1978 | Cosentino et al. | |
| 4,129,128 A | 12/1978 | McFarlane | |
| 4,133,312 A | 1/1979 | Burd | |
| 4,142,527 A | 3/1979 | Garcia | |
| 4,161,177 A | 7/1979 | Fuchs | |
| D252,822 S | 9/1979 | McFarlane | |
| 4,170,993 A | 10/1979 | Alvarez | |
| 4,193,174 A | 3/1980 | Stephens | |
| 4,194,504 A | 3/1980 | Harms et al. | |
| D256,162 S | 7/1980 | Haerr et al. | |
| 4,224,937 A | 9/1980 | Gordon | |
| 4,230,109 A | 10/1980 | Geiss | |
| 4,250,880 A | 2/1981 | Gordon | |
| 4,275,721 A | 6/1981 | Olson | |
| 4,314,568 A | 2/1982 | Loving | |
| 4,316,461 A | 2/1982 | Marais et al. | |
| 4,324,236 A | 4/1982 | Gordon et al. | |
| 4,326,519 A | 4/1982 | D'Alo et al. | |
| 4,333,468 A | 6/1982 | Geist | |
| 4,362,156 A | 12/1982 | Feller, Jr. et al. | |
| 4,392,853 A | 7/1983 | Muto | |
| 4,397,647 A | 8/1983 | Gordon | |
| 4,398,757 A | 8/1983 | Floyd et al. | |
| 4,405,163 A | 9/1983 | Voges et al. | |
| 4,405,312 A | 9/1983 | Gross et al. | |
| 4,435,174 A | 3/1984 | Redmond et al. | |
| 4,435,175 A * | 3/1984 | Friden | A61M 25/02 128/DIG. 26 |
| 4,439,193 A | 3/1984 | Larkin | |
| D273,993 S | 5/1984 | Schulte et al. | |
| 4,449,975 A | 5/1984 | Perry | |
| 4,453,933 A | 6/1984 | Speaker | |
| 4,470,410 A | 9/1984 | Elliott | |
| 4,474,559 A | 10/1984 | Steiger | |
| 4,480,639 A | 11/1984 | Peterson et al. | |
| 4,484,913 A | 11/1984 | Swauger | |
| 4,516,968 A | 5/1985 | Marshall et al. | |
| 4,517,971 A | 5/1985 | Sorbonne | |
| 4,561,857 A | 12/1985 | Sacks | |
| 4,563,177 A | 1/1986 | Kamen | |
| 4,585,435 A | 4/1986 | Vaillancourt | |
| 4,585,444 A | 4/1986 | Harris | |
| 4,631,056 A | 12/1986 | Dye | |
| 4,632,670 A | 12/1986 | Mueller, Jr. | |
| 4,633,863 A | 1/1987 | Filips et al. | |
| 4,645,492 A | 2/1987 | Weeks | |
| 4,650,473 A | 3/1987 | Bartholomew et al. | |
| 4,660,555 A | 4/1987 | Payton | |
| 4,666,434 A | 5/1987 | Kaufman | |
| 4,669,458 A | 6/1987 | Abraham et al. | |
| 4,693,710 A | 9/1987 | McCool | |
| 4,711,636 A | 12/1987 | Bierman | |
| 4,723,948 A | 2/1988 | Clark et al. | |
| 4,737,143 A | 4/1988 | Russell | |
| 4,742,824 A | 5/1988 | Payton et al. | |
| 4,743,231 A | 5/1988 | Kay et al. | |
| 4,752,292 A | 6/1988 | Lopez et al. | |
| 4,792,163 A | 12/1988 | Kulle | |
| 4,795,429 A | 1/1989 | Feldstein | |
| 4,826,486 A | 5/1989 | Palsrok et al. | |
| 4,834,702 A | 5/1989 | Rocco | |
| 4,834,716 A | 5/1989 | Ogle, II | |
| 4,838,858 A | 6/1989 | Wortham et al. | |
| D302,304 S | 7/1989 | Kulle et al. | |
| 4,846,807 A | 7/1989 | Safadago | |
| 4,852,844 A | 8/1989 | Villaveces | |
| 4,857,058 A | 8/1989 | Payton | |
| 4,863,432 A | 9/1989 | Kvalo | |
| 4,878,897 A | 11/1989 | Katzin | |
| 4,880,412 A | 11/1989 | Weiss | |
| 4,895,570 A | 1/1990 | Larkin | |
| 4,897,082 A | 1/1990 | Erskine | |
| 4,898,587 A | 2/1990 | Mera | |
| 4,919,654 A | 4/1990 | Kalt | |
| 4,934,375 A | 6/1990 | Cole et al. | |
| 4,941,882 A | 7/1990 | Ward et al. | |
| 4,955,864 A | 9/1990 | Hajduch | |
| 4,966,582 A | 10/1990 | Sit et al. | |
| 4,976,698 A | 12/1990 | Stokley | |
| 4,976,700 A | 12/1990 | Tollini | |
| 4,981,469 A | 1/1991 | Whitehouse et al. | |
| 4,981,475 A | 1/1991 | Haindl | |
| 4,997,421 A | 3/1991 | Palsrok et al. | |
| 5,024,665 A | 6/1991 | Kaufman | |
| 5,037,397 A | 8/1991 | Kalt et al. | |
| 5,037,398 A | 8/1991 | Buchanan | |
| 5,037,405 A | 8/1991 | Crosby | |
| 5,074,847 A | 12/1991 | Greenwell et al. | |
| D323,390 S | 1/1992 | Paine et al. | |
| 5,084,026 A | 1/1992 | Shapiro | |
| 5,098,048 A | 3/1992 | Chen | |
| 5,105,807 A | 4/1992 | Kahn et al. | |
| 5,112,313 A | 5/1992 | Sallee | |
| 5,116,324 A | 5/1992 | Brierley et al. | |
| 5,120,320 A | 6/1992 | Fayngold | |
| 5,135,506 A | 8/1992 | Gentelia et al. | |
| 5,137,519 A | 8/1992 | Littrell et al. | |
| 5,147,322 A | 9/1992 | Bowen et al. | |
| 5,156,641 A | 10/1992 | White | |
| 5,163,913 A * | 11/1992 | Rantanen-Lee et al. | 604/177 |
| 5,167,630 A | 12/1992 | Paul | |
| 5,192,273 A | 3/1993 | Bierman et al. | |
| 5,192,274 A | 3/1993 | Bierman | |
| 5,195,981 A | 3/1993 | Johnson | |
| 5,215,532 A | 6/1993 | Atkinson | |
| 5,238,010 A | 8/1993 | Grabenkort et al. | |
| 5,248,306 A | 9/1993 | Clark et al. | |

(56) References Cited

U.S. PATENT DOCUMENTS

| | | | |
|---|---|---|---|
| 5,263,943 A | 11/1993 | Vanderbrook | |
| 5,267,967 A | 12/1993 | Schneider | |
| 5,290,248 A | 3/1994 | Bierman et al. | |
| 5,306,253 A * | 4/1994 | Brimhall | 604/165.03 |
| 5,306,256 A | 4/1994 | Jose | |
| D347,060 S | 5/1994 | Bierman | |
| 5,314,411 A | 5/1994 | Bierman et al. | |
| 5,328,487 A | 7/1994 | Starchevich | |
| 5,330,438 A | 7/1994 | Gollobin et al. | |
| 5,336,195 A | 8/1994 | Daneshvar | |
| 5,344,414 A | 9/1994 | Lopez et al. | |
| 5,354,282 A | 10/1994 | Bierman | |
| 5,356,379 A | 10/1994 | Vaillancourt | |
| 5,356,391 A | 10/1994 | Stewart | |
| 5,370,627 A | 12/1994 | Conway | |
| 5,380,293 A | 1/1995 | Grant | |
| 5,380,294 A | 1/1995 | Persson | |
| 5,380,301 A | 1/1995 | Prichard et al. | |
| 5,382,239 A | 1/1995 | Orr et al. | |
| 5,382,240 A | 1/1995 | Lam | |
| 5,395,344 A | 3/1995 | Beisang, III et al. | |
| 5,413,120 A | 5/1995 | Grant | |
| 5,413,562 A | 5/1995 | Swauger | |
| D359,120 S | 6/1995 | Sallee et al. | |
| 5,456,671 A | 10/1995 | Bierman | |
| 5,470,321 A | 11/1995 | Forster et al. | |
| D364,922 S | 12/1995 | Bierman | |
| 5,484,425 A | 1/1996 | Fischell et al. | |
| 5,496,283 A | 3/1996 | Alexander | |
| 5,507,535 A | 4/1996 | McKamey et al. | |
| 5,531,695 A | 7/1996 | Swisher | |
| D375,355 S | 11/1996 | Bierman | |
| D375,356 S | 11/1996 | Bierman | |
| 5,577,516 A | 11/1996 | Schaeffer | |
| 5,578,013 A | 11/1996 | Bierman | |
| D377,831 S | 2/1997 | Bierman | |
| 5,605,546 A | 2/1997 | Wolzinger et al. | |
| 5,620,427 A | 4/1997 | Werschmidt et al. | |
| 5,626,565 A | 5/1997 | Landis et al. | |
| 5,643,217 A | 7/1997 | Dobkin | |
| 5,664,581 A | 9/1997 | Ashley | |
| 5,681,290 A | 10/1997 | Alexander | |
| 5,685,859 A | 11/1997 | Kornerup | |
| 5,686,096 A | 11/1997 | Khan et al. | |
| 5,690,616 A | 11/1997 | Mogg | |
| 5,690,617 A | 11/1997 | Wright | |
| 5,693,032 A | 12/1997 | Bierman | |
| 5,702,371 A | 12/1997 | Bierman | |
| 5,722,959 A | 3/1998 | Bierman | |
| 5,728,053 A | 3/1998 | Calvert | |
| 5,755,225 A | 5/1998 | Hutson | |
| 5,800,402 A | 9/1998 | Bierman | |
| 5,800,410 A | 9/1998 | Gawreluk | |
| 5,810,781 A | 9/1998 | Bierman | |
| 5,814,021 A | 9/1998 | Balbierz | |
| D399,954 S | 10/1998 | Bierman | |
| 5,827,230 A | 10/1998 | Bierman | |
| 5,827,239 A | 10/1998 | Dillon et al. | |
| 5,833,666 A | 11/1998 | Davis et al. | |
| 5,833,667 A | 11/1998 | Bierman | |
| 5,855,591 A | 1/1999 | Bierman | |
| 5,885,251 A | 3/1999 | Luther | |
| 5,885,254 A | 3/1999 | Matyas | |
| 5,897,519 A | 4/1999 | Shesol et al. | |
| 5,947,931 A | 9/1999 | Bierman | |
| 6,050,934 A | 4/2000 | Mikhail et al. | |
| D425,619 S | 5/2000 | Bierman | |
| 6,099,509 A | 8/2000 | Brown, Jr. et al. | |
| 6,113,577 A | 9/2000 | Hakky et al. | |
| 6,132,398 A | 10/2000 | Bierman | |
| 6,132,399 A | 10/2000 | Shultz | |
| 6,139,532 A | 10/2000 | Howell et al. | |
| D433,503 S | 11/2000 | Powers et al. | |
| 6,213,979 B1 | 4/2001 | Bierman | |
| 6,213,996 B1 | 4/2001 | Jepson et al. | |
| 6,224,571 B1 | 5/2001 | Bierman | |
| 6,228,064 B1 | 5/2001 | Abita et al. | |
| 6,231,547 B1 | 5/2001 | O'Hara | |
| 6,231,548 B1 | 5/2001 | Bassett | |
| 6,258,066 B1 | 7/2001 | Urich | |
| 6,270,086 B1 | 8/2001 | Lloyd | |
| 6,283,945 B1 | 9/2001 | Bierman | |
| 6,290,676 B1 | 9/2001 | Bierman | |
| 6,332,874 B1 | 12/2001 | Eliasen et al. | |
| 6,361,523 B1 | 3/2002 | Bierman | |
| 6,375,639 B1 | 4/2002 | Duplessie et al. | |
| 6,413,240 B1 | 7/2002 | Bierman et al. | |
| 6,428,515 B1 | 8/2002 | Bierman et al. | |
| 6,428,516 B1 | 8/2002 | Bierman | |
| 6,436,073 B1 | 8/2002 | Von Teichert | |
| 6,447,485 B2 | 9/2002 | Bierman | |
| 6,447,486 B1 | 9/2002 | Tollini | |
| 6,471,676 B1 | 10/2002 | DeLegge et al. | |
| 6,482,183 B1 | 11/2002 | Pausch et al. | |
| 6,491,664 B2 | 12/2002 | Bierman | |
| 6,500,154 B1 | 12/2002 | Hakky et al. | |
| D469,530 S | 1/2003 | Gomez | |
| D470,936 S | 2/2003 | Bierman | |
| 6,517,522 B1 | 2/2003 | Bell et al. | |
| 6,551,285 B1 | 4/2003 | Bierman | |
| 6,572,588 B1 | 6/2003 | Bierman et al. | |
| 6,582,403 B1 | 6/2003 | Bierman et al. | |
| 6,616,635 B1 | 9/2003 | Bell et al. | |
| 6,626,890 B2 | 9/2003 | Nguyen et al. | |
| 6,652,487 B1 | 11/2003 | Cook | |
| 6,663,600 B2 | 12/2003 | Bierman et al. | |
| 6,673,046 B2 | 1/2004 | Bierman et al. | |
| 6,689,104 B2 | 2/2004 | Bierman | |
| D492,411 S | 6/2004 | Bierman | |
| 6,770,055 B2 | 8/2004 | Bierman et al. | |
| 6,786,892 B2 | 9/2004 | Bierman | |
| 6,809,230 B2 | 10/2004 | Hancock et al. | |
| 6,824,527 B2 | 11/2004 | Gollobin | |
| 6,827,705 B2 | 12/2004 | Bierman | |
| 6,827,706 B2 | 12/2004 | Tollini | |
| 6,827,707 B2 | 12/2004 | Wright et al. | |
| 6,834,652 B2 | 12/2004 | Altman | |
| 6,837,875 B1 | 1/2005 | Bierman | |
| 6,866,652 B2 | 3/2005 | Bierman | |
| D503,977 S | 4/2005 | Bierman | |
| 6,951,550 B2 | 10/2005 | Bierman | |
| 6,972,003 B2 | 12/2005 | Bierman et al. | |
| 6,979,320 B2 | 12/2005 | Bierman | |
| 6,981,969 B2 | 1/2006 | Chavez et al. | |
| 7,014,627 B2 | 3/2006 | Bierman | |
| 7,018,362 B2 | 3/2006 | Bierman et al. | |
| 7,070,580 B2 | 7/2006 | Nielsen | |
| 7,090,660 B2 | 8/2006 | Roberts et al. | |
| D528,206 S | 9/2006 | Bierman | |
| 7,144,387 B2 * | 12/2006 | Millerd | 604/177 |
| 7,153,291 B2 | 12/2006 | Bierman | |
| 7,354,421 B2 | 4/2008 | Bierman | |
| 7,491,190 B2 | 2/2009 | Bierman et al. | |
| 7,935,083 B2 * | 5/2011 | Bierman et al. | 604/174 |
| 2002/0068904 A1 | 6/2002 | Bierman et al. | |
| 2002/0099360 A1 | 7/2002 | Bierman | |
| 2002/0133121 A1 | 9/2002 | Bierman | |
| 2003/0055382 A1 | 3/2003 | Schaeffer | |
| 2003/0163096 A1 * | 8/2003 | Swenson et al. | 604/263 |
| 2003/0181870 A1 | 9/2003 | Bressler et al. | |
| 2003/0229313 A1 | 12/2003 | Bierman | |
| 2004/0102736 A1 | 5/2004 | Bierman | |
| 2004/0111067 A1 | 6/2004 | Kirchhofer | |
| 2004/0204685 A1 | 10/2004 | Wright et al. | |
| 2005/0096606 A1 | 5/2005 | Millerd | |
| 2005/0182367 A1 | 8/2005 | Walborn | |
| 2005/0215953 A1 | 9/2005 | Rossen | |
| 2005/0288635 A1 | 12/2005 | Davis et al. | |
| 2006/0015076 A1 | 1/2006 | Heinzerling et al. | |
| 2006/0064063 A1 | 3/2006 | Bierman | |
| 2006/0079740 A1 | 4/2006 | Silver et al. | |
| 2006/0135944 A1 | 6/2006 | Bierman | |
| 2006/0184127 A1 | 8/2006 | Bierman | |
| 2006/0184129 A1 | 8/2006 | Bierman | |

(56) References Cited

U.S. PATENT DOCUMENTS

| | | |
|---|---|---|
| 2006/0217669 A1 | 9/2006 | Botha |
| 2006/0247577 A1 | 11/2006 | Wright |
| 2006/0264836 A1* | 11/2006 | Bierman ............... 604/180 |
| 2006/0270994 A1 | 11/2006 | Bierman |
| 2006/0270995 A1 | 11/2006 | Bierman |
| 2007/0016166 A1 | 1/2007 | Thistle |
| 2007/0016167 A1 | 1/2007 | Smith et al. |
| 2007/0250021 A1 | 10/2007 | Brimhall et al. |
| 2008/0045905 A1 | 2/2008 | Chawki |
| 2008/0300543 A1* | 12/2008 | Abriles et al. ............. 604/162 |
| 2010/0049139 A1 | 2/2010 | Kiyono et al. |
| 2010/0298777 A1 | 11/2010 | Nishtala |
| 2012/0265147 A1 | 10/2012 | Andino et al. |

FOREIGN PATENT DOCUMENTS

| | | |
|---|---|---|
| CA | 2690234 A1 | 12/2008 |
| DE | 2341297 A1 | 4/1975 |
| EP | 0114677 A2 | 8/1984 |
| EP | 0169704 A1 | 1/1986 |
| EP | 0247590 A2 | 12/1987 |
| EP | 0263789 A1 | 4/1988 |
| EP | 0356683 A1 | 3/1990 |
| EP | 0367549 A2 | 5/1990 |
| EP | 0720836 A2 | 7/1996 |
| FR | 2922458 A1 | 4/2009 |
| GB | 2063679 A | 6/1981 |
| GB | 2086466 A | 5/1982 |
| GB | 2178811 A | 2/1987 |
| WO | 9005559 A1 | 5/1990 |
| WO | 9421319 A1 | 9/1994 |
| WO | 9715337 A1 | 5/1997 |
| WO | WO 99/55409 | 11/1999 |
| WO | WO 2004/016309 | 2/2004 |
| WO | 2009/032008 A2 | 3/2009 |
| WO | 2010/132837 A1 | 11/2010 |

OTHER PUBLICATIONS

Written Opinion of the International Searching Authority from related International Application No. PCT/US2011/026897, mailed Apr. 26, 2011, in 5 pages.

AU 2010303477 filed Oct. 6, 2010 Examiner's Search Report dated Oct. 22, 2015.

Cravens, et al. "Urinary Catheter Management" American Family Physician, vol. 61, No. 2, pp. MDG 000273-MDG 000282, dated Jan. 15, 2000.

Dale® Foley Catheter Holder brochure, pp. MDG 000344-MDG 000346, 2002.

Expert Discusses Strategies to Prevent CAUTIs, Infection Control Today, pp. MDG 000603-MDG-000609, Jun. 2005.

Grip-Lok Universal Tubing Securement brochure, pp. MDG 000364-MDG 000366, 2005-2006.

Grip-LokTM Universal Tubing Securement brochure, pp. MDG 000348-MDG 000349, Jun. 12, 2012.

M.C. Johnson Co., Gath-Secure®—http://www.mcjohnson.com/cath-secure.html, last accessed Jun. 12, 2012.

PCT/US2007/077302 filed Aug. 30, 2007 International Search Report dated Mar. 28, 2008.

PCT/US2010/035004 filed May 14, 2010 International Search Report and Written Opinion dated Jul. 21, 2010.

PCT/US2010/051664 tiled Oct. 6, 2010 International Search Report and Written Opinion dated Dec. 2, 2010.

U.S. Appl. No. 13/320,381, filed Feb. 27, 2012 Final Office Action dated Dec. 17, 2015.

U.S. Appl. No. 13/320,381, filed Feb. 27, 2012 Non-Final Office Action dated Aug. 26, 2015.

U.S. Appl. No. 13/415,644, filed Aug. 3, 2012, Advisory Action dated Sep. 24, 2015.

U.S. Appl. No. 13/415,644, filed Aug. 3, 2012, Non Final Office Action dated Jun. 29, 2015.

U.S. Appl. No. 13/498,121, filed Jul. 3, 2012 Final Office Action dated Nov. 5, 2015.

U.S. Pat. No. 5,827,230 National Patent Services, Search Report re Patent Validity Study pp. MDG 001319-MDG 001320, dated May 23, 2006.

U.S. Appl. No. 13/320,381, filed Feb. 27, 2012 Non-Final Office Action dated Jul. 29, 2016.

U.S. Appl. No. 13/415,644, filed Aug. 3, 2012, Examiner's Answer dated Jun. 15, 2016.

U.S. Appl. No. 13/498,121, filed Jul. 3, 2012 Non-Final Office Action dated Jun. 3, 2016.

CA 2775571 filed Mar. 27, 2012 Office Action dated Aug. 8, 2016.

U.S. Appl. No. 13/498,121, filed Jul. 3, 2012 Final Office Action dated Dec. 15, 2016.

* cited by examiner

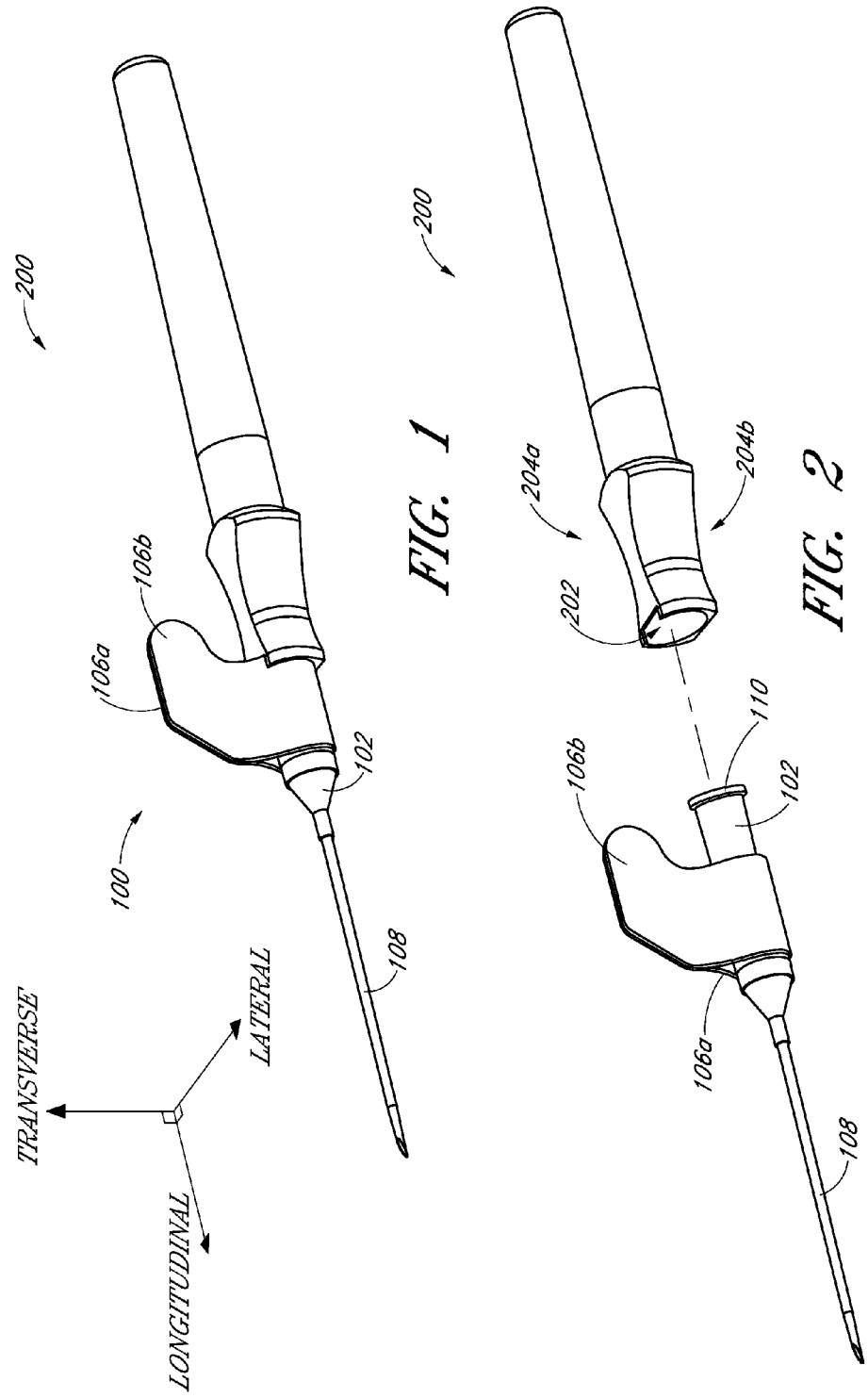

MEDICAL ARTICLE WITH ROTATABLE WINGS

CROSS-REFERENCE TO RELATED APPLICATIONS

This application is the National Stage of International Application No. PCT/US2011/026897, filed on Mar. 2, 2011, entitled "MEDICAL ARTICLE WITH ROTATABLE WINGS," which claims priority under 35 U.S.C. §119(e) to U.S. Provisional Application No. 61/310,223, filed Mar. 3, 2010, entitled "MEDICAL ARTICLE WITH ROTATABLE WINGS," both of which are hereby incorporated by reference in their entirety.

BACKGROUND

Field of the Invention

This invention relates to a medical article used to provide access to the vasculature of a patient. More particularly, this invention relates to a medical article with wings configured to stabilize the medical article on the patient.

Description of the Related Art

Medical professionals routinely require access to the vasculature of a patient for delivery or withdrawal of fluids to or from the patient's bloodstream. When such access is required over any period of time, it is common to introduce a catheter or similar medical article into the bloodstream of the patient to provide reusable access, for instance in order to deliver medication and/or fluids directly into the bloodstream of the patient.

In intravenous applications, the catheter is generally short and includes a fitting, for example, a luer connector, at one end that is designed for attachment to another medical line or another medical article. Such a connector may also include a spin nut to lock the medical line to the catheter. In this way the same catheter may be connected to and released from different medical lines in order to exchange the medical lines without the need to introduce multiple intravenous catheters. In some cases, an extension set comprising a medical tube with a spin nut at one end can be connected to the catheter, so that the free end of the extension set can be attached to another medical line or system as desired, at a location further away from the insertion site than the catheter hub.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be stabilized on the patient in a variety of ways. Most commonly, the medical provider may attempt to restrict movement of the catheter by securing the distal end of the catheter, or a portion of a medical device connected to the catheter such as a connector fitting, to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

SUMMARY OF THE INVENTION

The devices, systems, and methods of the present invention have several features, no single one of which is solely responsibly for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide several advantages over other medical articles.

One aspect of the present invention is a medical article for use in providing access to a patient's vasculature. The medical article includes an elongated body and a pair of wings extending away from the elongated body. The elongated body has a longitudinal axis, a distal end, and a proximal end. At least one of the pair of wings is configured to rotate about the longitudinal axis of the elongated body between at least a first configuration and a second configuration.

Another aspect of the present invention is a medical article for use in providing access to a patient's vasculature. The medical article includes an elongated body, a housing, and a wing extending away from the elongated body. The elongated body has a longitudinal axis, a distal end, and a proximal end. The housing is disposed around at least a portion of the elongated body and defines a channel between the housing and the elongated body. The wing is configured to rotate about the longitudinal axis of the elongated body between at least a first configuration and a second configuration with at least a portion of the wing disposed within the channel.

Yet another aspect of the present invention is a method for introducing a medical line into a patient's vasculature. The method includes providing a handpiece including a slot and providing a medical article including an elongated body, a pair of wings extending from the elongated body, and a catheter. The elongated body has a longitudinal axis, a distal end, and a proximal end. Each wing is rotatable about the longitudinal axis of the elongated body between at least a first configuration and a second configuration and the catheter extends from the elongated body in a direction substantially parallel to the longitudinal axis of the elongated body. The method also includes positioning at least a portion of each of the wings within the slot of the handpiece to inhibit free rotation of the wings from the first configuration towards the second configuration.

Another aspect of the present invention is a medical article for use in providing access to a patient's vasculature. The medical article includes an elongated body having a longitudinal axis and a pair of wings extending from the elongated body. The wings are releasably attachable to one another and configured to independently rotate about the longitudinal axis of the elongated body between at least a first configuration and a second configuration upon detachment of the wings from one another.

BRIEF DESCRIPTION OF THE DRAWINGS

The above mentioned and other features of the invention will now be described with reference to the drawings of several embodiments of the present stabilization system. The illustrated embodiments of the stabilization system are intended to illustrate, but not to limit the invention. The drawings contain the following figures:

FIG. 1 is a perspective view of a medical article according to a preferred embodiment of the present invention. The medical article is partially inserted into a handpiece.

FIG. 2 is a perspective view of the medical article and handpiece of FIG. 1 with the medical article disengaged from the handpiece.

DETAILED DESCRIPTION OF CERTAIN EMBODIMENTS

Figure 3:
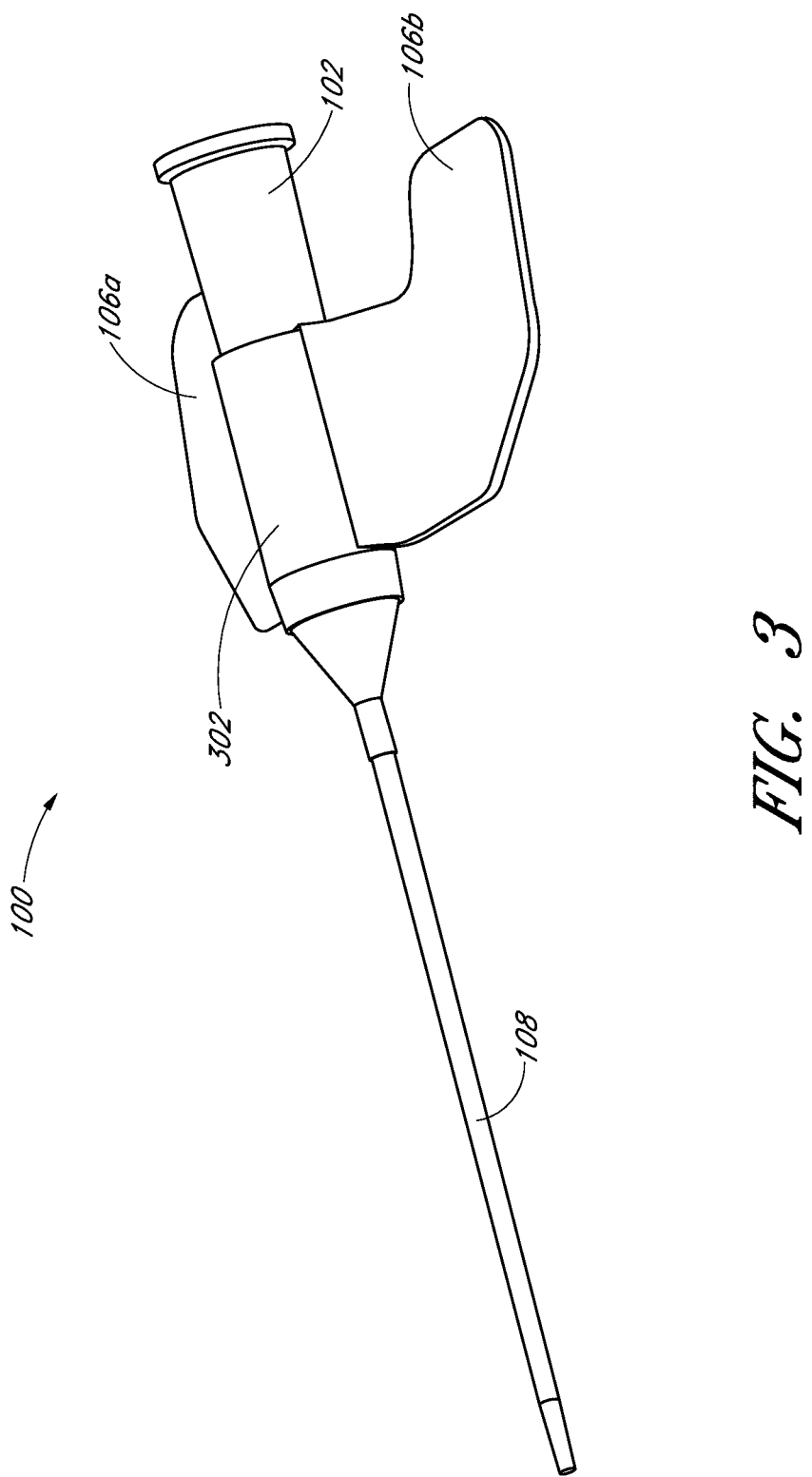
FIG. 3 is a perspective view of the medical article of FIG. 1 with the wings shown in a down configuration.

The following description and the accompanying figures, which describe and show the preferred embodiments, are made to demonstrate several possible configurations that a medical article can take to include various aspects and features of the invention. Some of the illustrated embodiments are shown with a handpiece that can be utilized by a health care provider to insert a medical article (e.g., a catheter) into a patient to provide access to the patient's vasculature. The illustration of the medical article in this context is not intended to limit the disclosed aspects and features of the invention to the specified embodiments or to usage only with the illustrated handpiece. Those of skill in the art will recognize that the disclosed aspects and features of the invention are not limited to any particular application.

To assist with the description of the components of the medical article, the following coordinate terms are used (see FIG. 1). A "longitudinal axis" is generally parallel to a portion of the catheter hub or medical article body, as well as parallel to the axis of the catheter. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present medical article, are used consistently with the description of the exemplary applications (e.g., the illustrative examples of the use applications). Thus, proximal and distal are used in reference to the center of the patient's body. The terms "upper," "lower," "top," "bottom," "underside," "upperside" and the like, which also are used to describe the present medical article, are used in reference to the illustrated orientation of the embodiment. For example, the term "upperside" is used to describe the portion of the medical article that is located above a lateral axis that passes through the longitudinal axis of the medical article. The term "underside" is used to describe the portion of the medical article that is located below a lateral axis that passes through the longitudinal axis of the medical article. Brief introductions to some of the features, which are common to the described embodiments of the medical articles, are now described.

The preferred embodiments of the present invention advantageously provide a medical article for providing access to a patient's vasculature. The medical article preferably has one or more wings configured to stabilize and/or secure the medical article relative to the patient's skin. The one or more wings of the medical article can be configured to rotate about the longitudinal axis of the medical article between at least a first configuration and a second configuration. The one or more wings can be configured to lock in place, relative to the body of the medical article, in one or more configurations. The wings can also be secured relative to the patient's skin to secure the medical article relative to the patient.

In each of the embodiments described below, the medical article has an elongated body. The elongated body includes a proximal end and a distal end with a catheter extending from the proximal end for insertion into a patient. A fitting can be positioned near the distal end to fluidly couple the elongated body to a medical line or an extension set. A housing can surround the elongated body and create a channel therebetween through which the pair of wings can move between at least a first configuration and a second configuration. In some embodiments, the wings and elongated body are joined by a living hinge that allows the wings to bend or rotate relative to the elongated body.

To facilitate a complete understanding of the illustrated embodiment, the remainder of the detailed description describes the medical article with reference to the attached figures, wherein like elements among the embodiments are referenced with like numerals throughout the following description.

Medical Article

Figure 5:
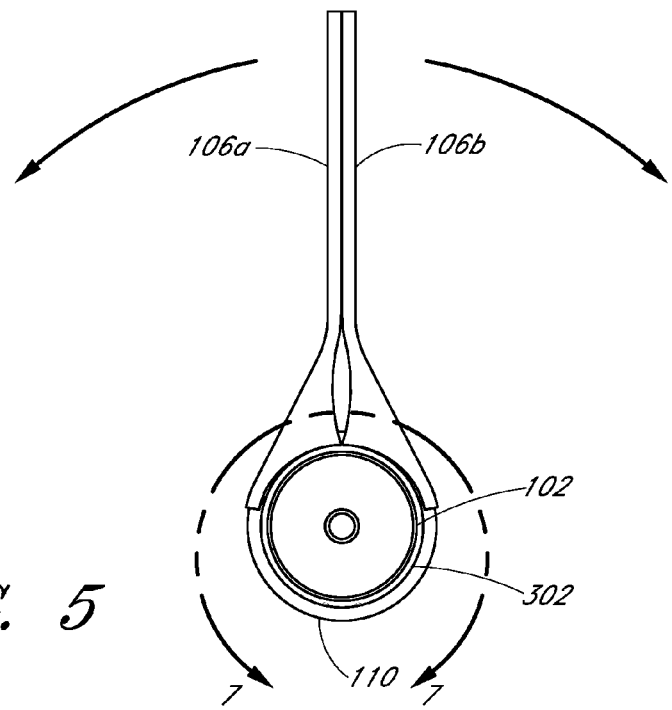
FIG. 5 is a front view of the medical article of FIG. 3 with the wings shown in an up configuration.
Figure 6:
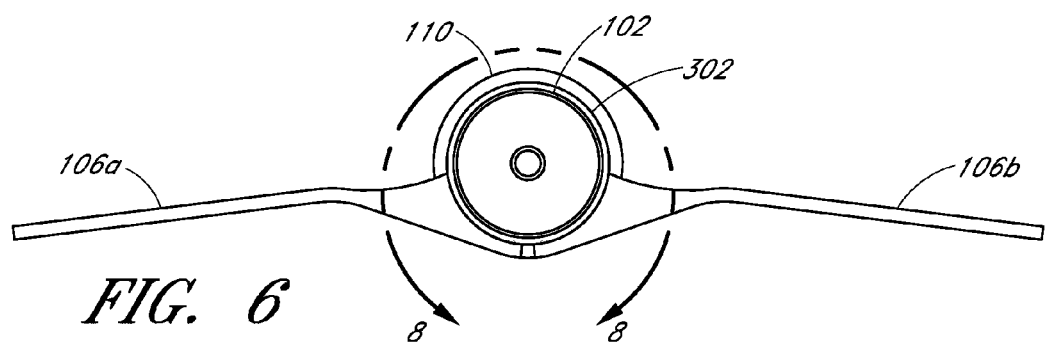
FIG. 6 is a front view of the medical article of FIG. 3 with the wings shown in the down configuration.
Figure 7:
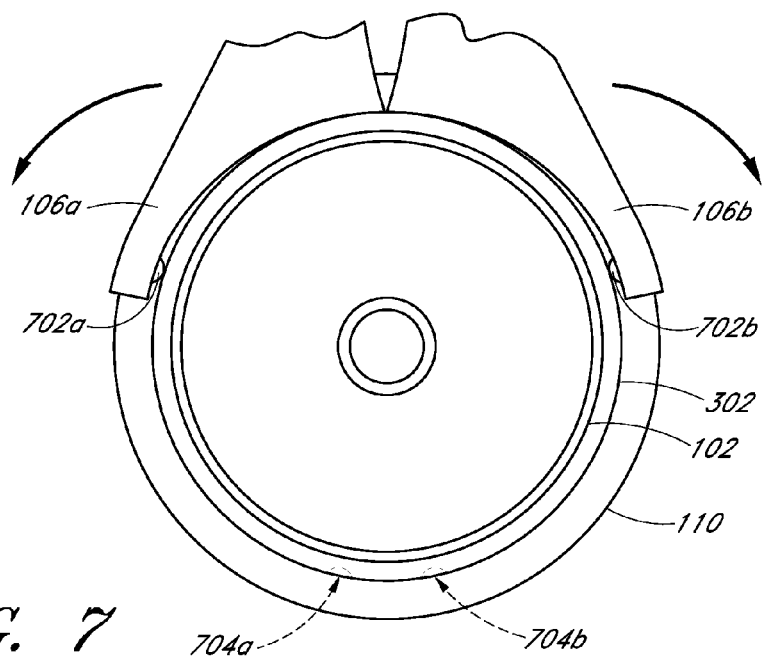
FIG. 7 is a close-up view of the elongated body and wings shown in FIG. 5.
Figure 8:
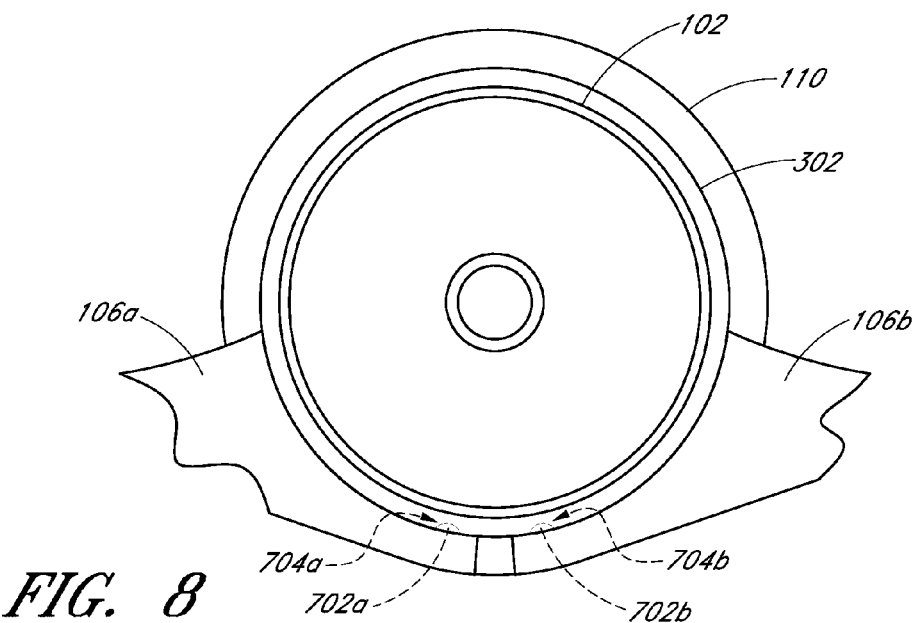
FIG. 8 is a close-up view of the elongated body and wings shown in FIG. 6.

FIG. 1 shows a perspective view of a medical article 100 partially inserted into a handpiece or catheter introducer 200. The medical article 100 includes an elongated body or hub 102, a catheter 108 extending from the elongated body 102 in a direction substantially parallel to the longitudinal axis of the medical article 100, and a pair of wings 106a, 106b extending in an outward direction from the hub 102. Wings 106a, 106b are shown extending generally parallel to the transverse axis of the medical article 100 and can be considered in an "up" configuration. When in the up configuration the wings 106a, 106b can be releasably attached to one another. Upon detachment from one another, the wings, 106a, 106b can rotate independently from one another relative to the longitudinal axis of the medical article 100 between at least the up configuration and a "down" configuration (see FIGS. 5 and 6). Alternatively, the wings 106a, 106b can be coupled or linked to one another such that rotation of one of the wings causes the other wing to rotate relative to the longitudinal axis of the medical article.

As shown in FIG. 2, the medical article 100 also includes a fitting 110 disposed near the distal end of the elongated body 102. The fitting 110 can comprise a luer connector or another fitting configured to connect the medical article 100 with a variety of other medical articles including medical lines, extension sets, other connector fittings, and the like. The medical article 100 can also include a one-way valve, membrane, or septum disposed within the elongated body 102. In some embodiments the one-way valve is disposed near the distal end of the medical article 100 or fitting 110 to permit the passage of fluid therethrough in a single direction, for example, into a patient.

The distal end of the medical article 100 can be partially inserted into handpiece 200 such that at least a portion of the wings 106a, 106b of the medical article abut the handpiece 200. The handpiece 200 can include a slot 202 configured to receive a portion of the wings 106a, 106b to inhibit or limit free rotation of the wings when they are partially received within the slot 202. The handpiece 200 can also include one or more contoured surfaces 204a, 204b to facilitate proper gripping of the handpiece 200. By such a configuration, the handpiece 200 and the elongated body 102 can cooperate to assist a medical professional in handling and placing the catheter 108 in a patient's vasculature.

Figure 4:
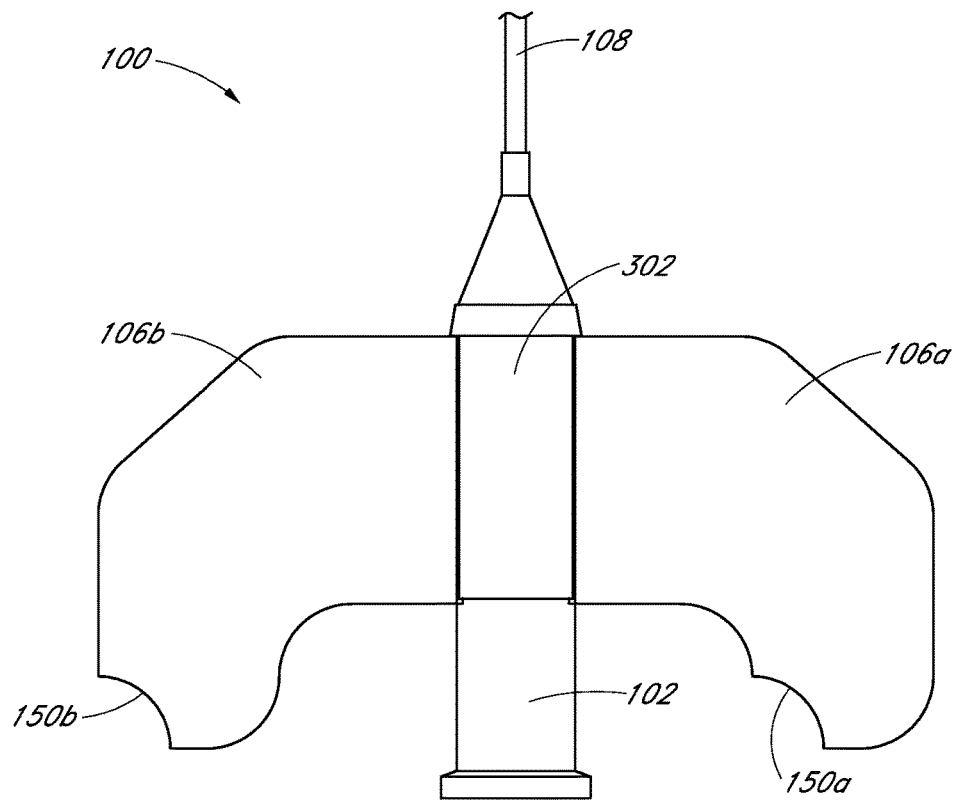
FIG. 4 is a top plan view of the medical article of FIG. 3.

As shown in FIGS. 3-11, the wings 106a, 106b can rotate relative to the elongated body 102 from the up configuration to the down configuration. FIGS. 3 and 4 show the wings 106a, 106b in the down configuration. The wings 106a, 106b can be configured to stabilize the medical article 100 on a patient when they are in the down configuration. The wings 106a, 106b can further be configured to secure the medical article relative to the patient. In some embodiments, the wings 106a, 106b can include an adhesive layer disposed over a portion of each wing to secure the wings to the patient. As discussed in more detail below, in other embodiments, the wings 106a, 106b can be taped to a patient to inhibit movement of the medical article 100 relative to the patient. When the wings 106a, 106b are secured to a patient, they can act to inhibit longitudinal, lateral, transverse, and rotational movement of the elongated body 102 relative to the patient.

The wings 106a, 106b can comprise various suitable materials including, for example, plastics or textiles. In some embodiments, the wings 106a, 106b can be biased to rotate away from one another upon detachment of the wings from one another. For example, the wings 106a, 106b can be spring-loaded to rotate relative to the longitudinal axis of the medical article 100. In some embodiments, the wings 106a, 106b can be joined with the medical article 100 by a living hinge that is configured to allow the wings to bend or rotate along the line of the hinge. In other embodiments, the wings 106a, 106b can be unbiased and manually rotatable (independently or together) relative to the medical article 100 by a medical professional. As shown in FIG. 4, the wings 106a, 106b can optionally include tabs 150a, 150b that a medical professional can use to separate the wings from one another and further manipulate the wings relative to the longitudinal axis of the elongated body 102.

The wings 106a, 106b can each form an angle of between about 0 degrees and about 30 degrees with the skin of the patient when they are in the down configuration. For example, the wings 106a, 106b can each form an angle of between about 5 degrees and about 10 degrees with the skin of the patient. This configuration can result in an offset of the elongated body 102 from a portion of the patient. The wings 106a, 106b can also be configured to stabilize the medical article 100 relative to the patient such that the longitudinal axis of the medical article 100 and the skin of the patient form an angle between about 5 degrees and about 35 degrees. This angle can facilitate a proper insertion of the catheter 108 into the patient's vasculature.

The needle of the catheter 108 includes a beveled tip. Preferably the bevel is aligned with one or more points on the medical article. For example, the bevel can be aligned with a 12 o'clock position of the elongated body 102 and/or housing 302. In some embodiments, the bevel and the wings 106a, 106b can be rotationally aligned about the longitudinal axis of the medical article 100. As illustrated in FIG. 1, the bevel can be aligned with the wings 106a, 106b in the up configuration. Aligning the bevel relative to the medical article can facilitate the proper placement of the bevel within a patient's vasculature.

As can be seen most clearly in FIGS. 5-8, in some embodiments, a housing 302 can be disposed around a portion of the elongated body 102 to form a channel between the housing and the elongated body. The housing 302 and wings 106a, 106b can include interengaging structure which when engaged limits or inhibits further rotation of the wings 106a, 106b relative to the body 102. For example, the housing 302 can include one or more detents 704a, 704b configured to receive protrusions 702a, 702b disposed on the wings 106a, 106b. Of course the housing 302 may include the protrusions 702a, 702b and the wings 106a, 106b may include the detents 704a, 704b.

The detents 704a, 704b and the protrusions 702a, 702b can be configured to releasably lock the wings 106a, 106b relative to the elongated body 102 when the protrusions are slid over and received within the detents. The detents 704a, 704b can act to limit the rotation of the wings 106a, 106b and/or to define a configuration for the wings, for example, the down configuration. In some embodiments, the wings 106a, 106b can be releasably locked relative to the elongated body 102 in the down configuration.

Figure 9:
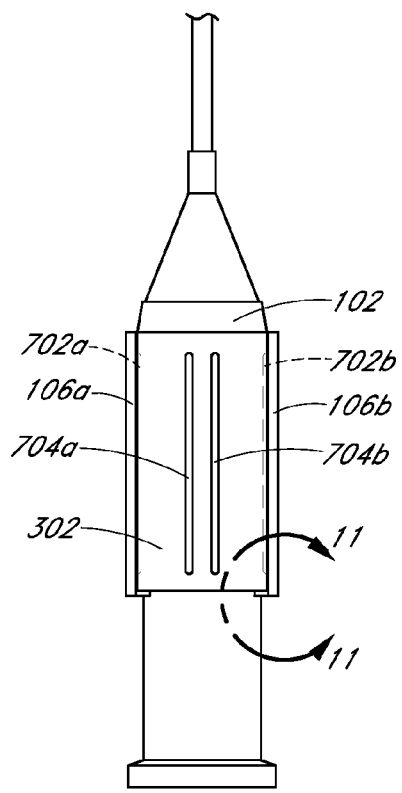
FIG. 9 is a bottom view of the medical article of FIG. 3 with the wings positioned in the up configuration.
Figure 10:
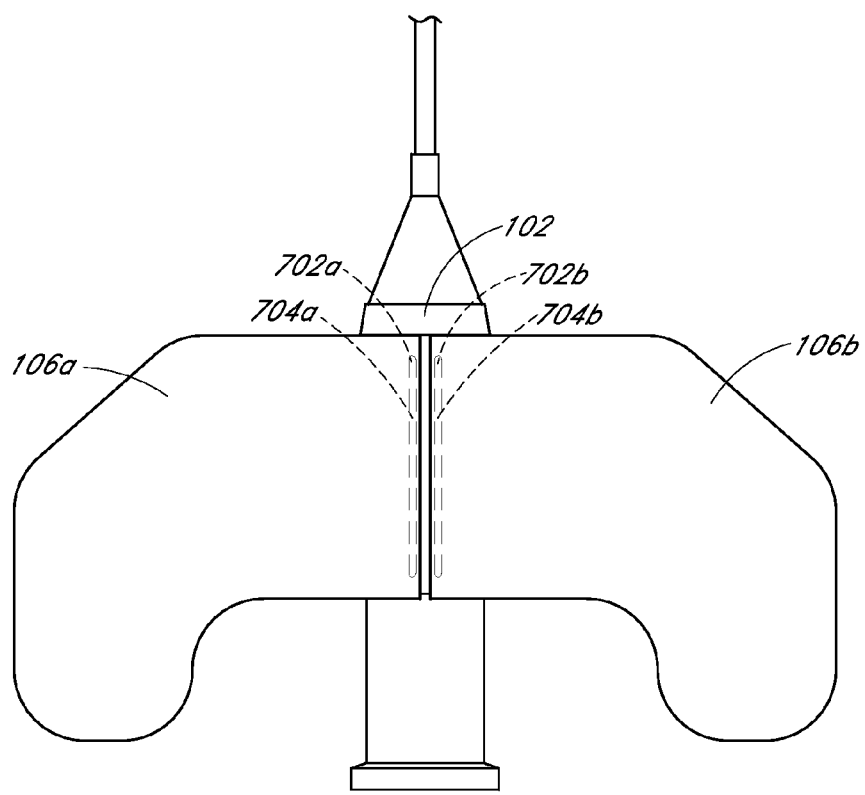
FIG. 10 is a bottom view of the medical article of FIG. 3 with the wings positioned in the down configuration.
Figure 11:
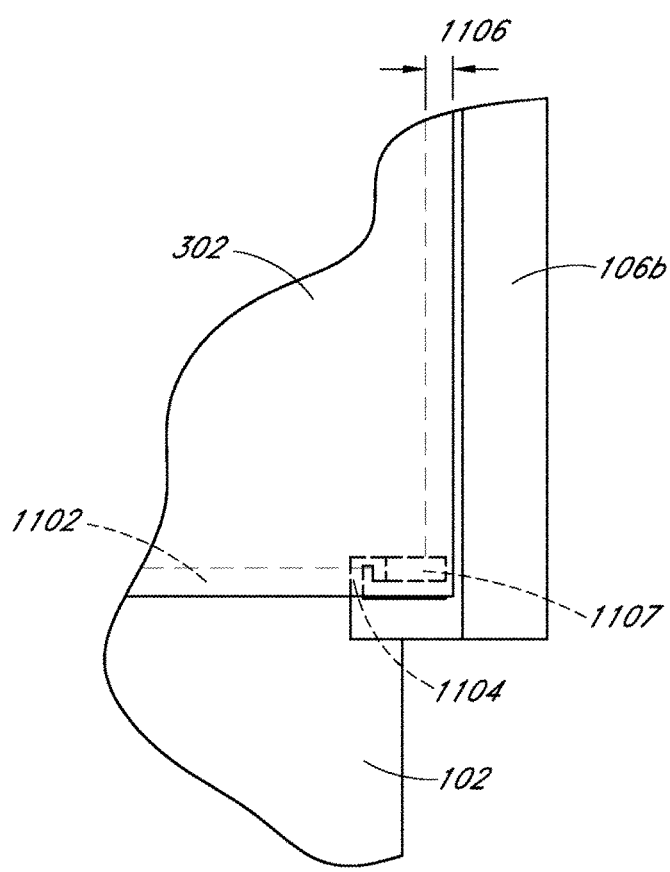
FIG. 11 is a close-up view of the elongated body and a wing shown in FIG. 9.

FIGS. 9-11 show bottom views of the medical article 100. In FIG. 9, the bottom of the medical article 100 is shown with the wings 106a, 106b positioned in the up configuration. The protrusions 702a, 702b are positioned outside the housing 302 and are offset from the detents 704a, 704b. FIG. 10 shows the wings 106a, 106b in the down configuration with the protrusions 702a, 702b received within the detents 704a, 704b to releasably lock the wings relative to the elongated body 102 in the down position.

FIG. 11 shows a close-up view of the elongated body 102, housing 302, and wing 106b shown in FIG. 9. The housing 302 can include a lip 1102 and the wing 106b can include a hook 1104 that is positioned between the housing 302 and the elongated body 102. The hook 1104 can move around the elongated body 102 as the wings 106a, 106b rotate relative to the longitudinal axis of the medical article. For example, the hook can engage the lip 1102 of the housing 302 as the hook 1104 can move in a channel or space 1107 between the housing 302 and the elongated body 102. FIG. 11 also illustrates an exemplary wall thickness 1106 of the housing 302.

Method of Use

Figure 12:
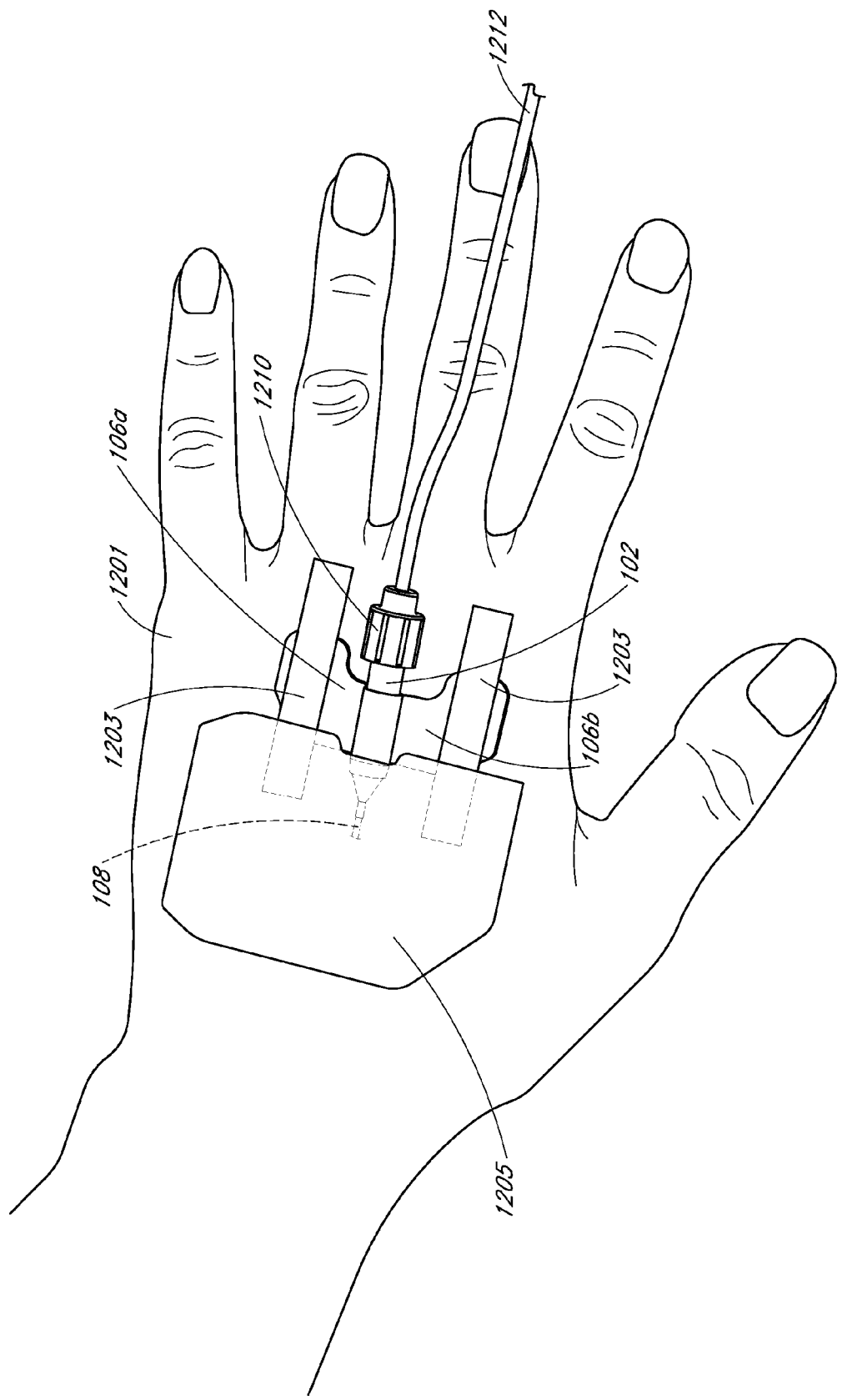
FIG. 12 is a perspective view of the medical article of FIG. 3 shown with the catheter portion inserted into a patient and secured to the patient's skin with adhesive strips.

The following method of use will be with reference principally to FIGS. 1, 2, and 12 and will be in the context of starting an intravenous ("I.V.") line using medical article 100 and handpiece 200. The discussion of one embodiment of a method of use is meant to augment the description of the invention above and both should be read together.

In starting an I.V. line, the medical professional begins by inserting the medical article 100 into the handpiece 200 as shown in FIG. 1. The medical professional then uses the medical article 100 and handpiece 200 to insert the catheter 108 into the vasculature of the patient 1201 with the beveled tip positioned up. The medical professional can then remove the medical article 100 from the handpiece 200 and discard the handpiece. The medical professional can then attach a connector 1210 to the fitting 110 to establish fluid communication between the medical article 100 and a medical line 1212.

Once the catheter 108 is inserted into the patient 1201 and the medical article 100 is connected to a medical line 1212, the medical professional can move the wings 106a, 106b to the down configuration. As discussed above, in some embodiments, the wings 106a, 106b can optionally be releasably locked relative to the elongated body 102. The medical professional can then secure the medical article 100 to the patient 1201 by placing adhesive strips 1203 over the wings 106a, 106b and/or by adhering the wings 106a, 106b directly to the patient's skin.

Finally, the medical professional can position a dressing or covering 1205, for example, a piece of Tegaderm™, over the insertion site to protect the site from infection. The covering 1205 can be provided separate from the medical article 100 or the covering 1205 can be integral with the medical article 100. For example, the covering 1205 can initially be disposed at least partially between the wings 106a, 106b when they are in the up configuration such that the covering 1205 is released as the wings are moved to the down configuration. In one embodiment, the covering 1205 is folded between the wings 106a, 106b in the up configuration such that the covering unfolds in the proximal direction when the wings 106a, 106b are moved to the down configuration. For example, the covering 1205 can be folded multiple times in an accordion or fan-like arrangement between the wings 106a, 106b such that the covering unfolds when the wings 106a, 106b are moved apart from one another.

The covering 1205 and the wings 106a, 106b can be formed as an integral, single piece. Alternatively, the covering 1205 and the wings 106a, 106b are formed separately and then attached together. In this case, the covering 1205 and the wings 106a, 106b may be attached by any means or mechanism that allows the covering 1205 to fold, bend, or rotate down over the insertion site area. Attachment means include glue or adhesive, a weld of the materials, heat sealing, mechanical fasteners such as staples or eyelets, or other such means of attachment.

The occlusive covering 1205 can be configured to be waterproof or otherwise impermeable to liquids and in some embodiments also restricts the flow of air. In other embodiments, the covering 1205 may be configured to be breathable, allowing air and/or moisture near an insertion site through to the other side of the covering 1205 and away from the insertion site, while keeping at least external moisture on the other side of the covering 1205 away from the insertion site. In some embodiments, the covering 1205 is impermeable to viruses and bacteria, and may comprise or be coated with an anti-bacterial or anti-microbial material. In some embodiments, the covering 1205 comprises or is coated with a waxy material. In some embodiments, the covering 1205 comprises a film which may or may not be transparent. Selection of a transparent film for use as the covering 1205 may allow a medical provider to see the insertion site and any administered catheter. In some embodiments, covering 1205 is absorbent.

The wings 106a, 106b can be used as a long-term solution to secure the medical article 100 relative to the patient 1201 until the catheter 108 is removed. Alternatively, the wings 106a, 106b can be used as a short-term or temporary solution to secure the medical article 100 relative to the patient 1201 until the medical article is secured relative to the patient by a different device or method.

The various embodiments of medical articles and techniques described above thus provide a number of ways to stabilize a medical article to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above but by a fair reading of the claims which follow.

What is claimed is:

1. A medical article for use in providing access to a patient's vasculature, the medical article comprising: a catheter hub having a longitudinal axis, a distal end, and a proximal end; a catheter continuously extending from the proximal end of the catheter hub, the catheter and the catheter hub together defining a continuous lumen; a housing surrounding the catheter hub, wherein a channel is defined between the housing and the catheter hub; the channel surrounding the catheter hub; and a pair of wings extending away from the catheter hub, at least a first wing of the pair of wings being configured to rotate about the longitudinal axis of the catheter hub between at least a first configuration and a second configuration, the first wing including a hook portion coupling the first wing to the housing, wherein at least a portion of the hook portion is disposed within the channel.

2. The medical article of claim 1, wherein the catheter includes a bevel disposed near a distal end of the catheter, the bevel and at least a portion of the first wing being rotationally aligned about the longitudinal axis of the catheter hub when the first wing is in the first configuration.

3. The medical article of claim 1, further comprising an adhesive layer disposed on at least a portion of one side of each wing of the pair of wings, the adhesive layer configured to releasably attach each wing of the pair of wings to a patient's skin.

4. The medical article of claim 1, wherein the catheter hub comprises a luer connector disposed near the distal end, the luer connector being configured to connect the catheter hub with a medical line.

5. The medical article of claim 1, wherein each wing of the pair of wings is configured to rotate independently from one another.

6. The medical article of claim 1, wherein rotation of one wing of the pair of wings rotates the other wing of the pair of wings.

7. The medical article of claim 1, wherein each wing of the pair of wings is spring-loaded and configured to be biased to rotate away from one another from the first configuration to the second configuration.

8. The medical article of claim 1, wherein at least one wing of the pair of wings includes a protrusion.

9. The medical article of claim 8, wherein the housing includes at least one detent configured to engage with the protrusion.

10. The medical article of claim 1, further comprising a handpiece including a slot, wherein at least a portion of the first wing is received within the slot when the first wing is in the first configuration.

11. The medical article of claim 10, wherein the slot inhibits free rotation of the first wing from the first configuration towards the second configuration.

12. The medical article of claim 10, wherein a proximal end of the catheter hub is received within the slot.

13. A medical article for use in providing access to a patient's vasculature, the medical article comprising: a catheter hub having a longitudinal axis and a distal end; a catheter continuously extending from a proximal end of the catheter hub, the catheter and the catheter hub together defining a continuous lumen; a housing surrounding the catheter hub, wherein a channel is defined between the housing and the catheter hub; the channel surrounding the catheter hub and a pair of wings extending from the catheter hub, wherein the wings are releasably attachable to one another and configured to independently rotate about the longitudinal axis of the catheter hub between at least a first configuration and a second configuration upon detachment of the wings from one another, wherein a first wing of the pair of wings includes a hook portion coupling the first wing to the housing, wherein at least a portion of the hook portion is disposed within the channel.

14. The medical article of claim 13, further comprising an adhesive layer disposed on at least a portion of one side of each wing of the pair of wings, the adhesive layer configured to releasably attach each wing of the pair of wings to a patient's skin.

15. The medical article of claim 13, wherein the catheter hub comprises a luer connector disposed near the distal end, the luer connector being configured to connect the catheter hub with a medical line.

16. A method, comprising: providing a handpiece including a slot, a first contoured surface and a second contoured surface, the first contoured surface and the second contoured surface forming a concave shape: providing a medical article, comprising: an elongated body having a longitudinal axis, a distal end, and a proximal end, a pair of wings extending from the elongated body, each wing having a portion adjacent the elongated body coupled thereto, the coupled portion of each wing of the pair of wings moving with respect to the elongated body from a first configuration to a second configuration, wherein the coupled portions are adjacent to one another in the second configuration, a housing surrounding the elongated body, wherein a channel is defined between the housing and the elongated body, the channel surrounding the catheter hub and a catheter extending from the proximal end of the elongated body in a direction substantially parallel to the longitudinal axis of the elongated body; and positioning at least a section of each wing of the pair of wings within the slot of the handpiece to inhibit free rotation of the pair of wings from the first configuration towards the second configuration and a hook portion coupling the first wing to the housing, wherein at least a portion of the hook portion is disposed within the channel.

17. The method of claim 16, further comprising removing the section of each wing of the pair of wings from the slot.

18. The method of claim 16, further comprising securing each wing of the pair of wings relative to a patient.

19. The method of claim 16, further comprising rotating each wing of the pair of wings from the first configuration to the second configuration.

\* \* \* \* \*